United States Patent [19]

Jacob

[11] Patent Number: 5,171,525
[45] Date of Patent: * Dec. 15, 1992

[54] PROCESS AND APPARATUS FOR DRY STERILIZATION OF MEDICAL DEVICES AND MATERIALS

[76] Inventor: Adir Jacob, 23 Juniper La., Framingham, Mass. 01701

[*] Notice: The portion of the term of this patent subsequent to Feb. 6, 2007 has been disclaimed.

[21] Appl. No.: 562,392

[22] Filed: Aug. 3, 1990

Related U.S. Application Data

[63] Continuation of Ser. No. 331,438, Mar. 31, 1989, Pat. No. 4,976,920, which is a continuation-in-part of Ser. No. 72,899, Jul. 14, 1987, Pat. No. 4,818,488, which is a continuation-in-part of Ser. No. 19,134, Feb. 25, 1987, Pat. No. 4,801,427.

[51] Int. Cl.⁵ .............................................. A61L 2/14
[52] U.S. Cl. ........................................ 422/23; 422/22; 422/292; 422/304; 422/906; 422/907; 250/424; 250/455.11; 250/492.1; 204/164
[58] Field of Search ................................ 422/22–23, 422/28, 33, 36–37, 906–907, 292, 304; 204/164, 295; 250/424, 455.1, 492.1, 496.1

[56] References Cited

U.S. PATENT DOCUMENTS

| | | | |
|---|---|---|---|
| Re. 30,505 | 2/1981 | Jacob | 156/643 |
| 3,536,602 | 10/1970 | Jones et al. | 204/164 |
| 3,701,628 | 10/1972 | Ashman et al. | 21/54 R |
| 3,753,651 | 8/1973 | Boucher | 21/54 R |
| 3,757,733 | 9/1973 | Reinberg | 118/49.5 |
| 3,879,597 | 4/1975 | Bersin et al. | 219/121 |
| 3,923,568 | 12/1975 | Bersin | 156/8 |
| 3,951,709 | 4/1976 | Jacob | 156/8 |
| 3,971,684 | 7/1976 | Muto | 156/13 |
| 3,994,793 | 11/1976 | Harvilchuck et al. | 204/192 |
| 4,026,742 | 5/1977 | Fujino | 156/643 |
| 4,028,155 | 6/1977 | Jacob | 156/643 |
| 4,030,967 | 6/1977 | Ingrey et al. | 156/643 |
| 4,073,669 | 2/1978 | Heinecke et al. | 156/643 |
| 4,163,891 | 8/1979 | Komatsu | 219/121 |
| 4,182,646 | 1/1980 | Zajac | 156/643 |
| 4,207,286 | 6/1980 | Boucher | 422/21 |
| 4,208,241 | 6/1980 | Harshbarger et al. | 156/643 |
| 4,210,813 | 7/1980 | Romanovsky et al. | 378/101 |
| 4,211,601 | 7/1980 | Mogab | 156/643 |
| 4,214,946 | 7/1980 | Forget et al. | 156/643 |
| 4,226,665 | 10/1980 | Mogab | 156/643 |
| 4,229,247 | 10/1980 | Chiu et al. | 156/643 |
| 4,255,230 | 3/9181 | Zajac | 156/643 |
| 4,256,534 | 3/1981 | Levinstein et al. | 156/643 |
| 4,264,409 | 4/1981 | Forget et al. | 156/643 |
| 4,267,013 | 5/1981 | Iida et al. | 156/643 |
| 4,298,443 | 11/1981 | Maydan | 204/192 E |
| 4,314,874 | 2/1982 | Abe et al. | 156/628 |
| 4,314,875 | 2/1982 | Flamm | 156/643 |
| 4,341,592 | 7/1982 | Shortes et al. | 156/643 |
| 4,341,616 | 7/1982 | Nagatomo et al. | 204/298 |
| 4,353,777 | 10/1982 | Jacob | 156/643 |
| 4,358,686 | 11/1982 | Kinoshita | 204/298 |
| 4,362,632 | 12/1982 | Jacob | 422/183.04 |
| 4,505,782 | 3/1985 | Jacob et al. | 156/643 |
| 4,569,895 | 2/1986 | Willett et al. | 430/70 |
| 4,643,876 | 2/1987 | Jacobs et al. | 422/23 |
| 4,756,882 | 7/1988 | Jacobs et al. | 422/23 |
| 4,898,715 | 2/1990 | Jacob | 422/22 |
| 4,957,606 | 9/1990 | Suvan | 422/186.28 |
| 4,976,920 | 12/1990 | Jacob | 422/22 |

FOREIGN PATENT DOCUMENTS 0207417 6/1985 European Pat. Off. .
56-148354 4/1980 Japan .

OTHER PUBLICATIONS

*Glow Discharge Polymerization Modes of Electric Discharge*, H. Yasuda, Journal of Polymer Science: Macromolecular Reviews, vol. 16, pp. 207–212, (Wiley, 1981).
*Plasma Treatment*, Peter W. Rose et al, Plastics Finishing and Decoration edited by Donatas Satas, pp. 90–100.

Primary Examiner—James C. Housel
Assistant Examiner—Lyle A. Alexander
Attorney, Agent, or Firm—Lahive & Cockfield

[57] ABSTRACT

A process for dry sterilization of medical or dental devices and materials in which these materials are subjected to an electrical discharge in a gaseous atmosphere to produce an active low temperature plasma for surface sterilization and treatment of the devices and materials.

27 Claims, 3 Drawing Sheets

PROCESS AND APPARATUS FOR DRY STERILIZATION OF MEDICAL DEVICES AND MATERIALS

This is a continuation of application Ser. No. 331,438, filed Mar. 31, 1989, now U.S. Pat. No. 4,976,920, filed Mar. 31, 1989 which is a Continuation-In-Part of U. S. patent application 072,899 filed Jul. 14, 1987, to be issued under U.S. Pat. No. 4,818,488 on Apr. 4, 1989 which is a Continuation-In-Part of U.S. patent application Ser. No. 019,134 filed Feb. 25, 1987, now issued to U.S. Pat. No. 4,801,427 issued Jan. 31, 1989.

BACKGROUND OF THE INVENTION

Modern medical and dental practice require the use of aseptic materials and devices, many of them meant for repeat use. In order to achieve this sterilization, processes are needed, at the manufacturer, and also at the hospitals or dental offices for treatment of reusable materials and devices.

Typical of materials which are reused in the hospital environment and require repeated sterilization are major surgical instrument trays, minor surgical kits, respiratory sets, fiber optics (endoscopes, proctoscopes, angioscopes, bronchioscopes) and breast pumps. Typical instruments and devices which are reused in a dental environment and require repeated sterilization are hand-pieces, dental mirrors, plastic tips, model impressions and fabrics.

There are a wide variety of medical devices and materials that are to be supplied from the manufacturer already packaged and sterile. Many of these devices and materials are disposable. Typical of this group are barrier packs, head coverups and gowns, gloves, sutures, syringes and catheters.

One major sterilization process in present use is that which employs ethylene oxide (EtO) gas in combination with Freon-12 ($CCl_2F_2$) at up to three atmospheres of pressure in a special shatter-proof sterilization chamber. This process, in order to achieve effective asepsis levels, requires exposure of the materials to the gas for at least one to three hours followed by a minimum of twelve hours, or longer, aeration period. The initial gas exposure time is relatively long because the sterilization is effected by alkylation of amino groups in the proteinaceous structure of any microorganism. EtO sterilization requires the attachment of the entire EtO molecule, a polyatomic structure containing seven atoms to the protein. This is accompanied by the requirement of hydrogen atom rearrangement on the protein to enable the attachment of EtO. Because of kinetic space-hindrance factors governing the attachment of such a bulky molecule, the process needs to be carried out at high pressure and be extended over a long period of time. It is, therefore, deemed very inefficient by the industry at large.

Perhaps the chief drawback to this system, however, is its dangerous toxicity. Ethylene-oxide (EtO) is a highly toxic material dangerous to humans. It was recently declared a carcinogen as well as a mutagen. It requires a very thorough aeration process following the exposure of the medical materials to the gas in order to flush away toxic EtO residues and other toxic liquid by-products like ethylene glycol and ethylene chlorohydrin. Unfortunately, it is a characteristic of the gas and the process that EtO and its toxic by-products tend to remain on the surface of the materials being treated. Accordingly, longer and longer flush (aeration) times are required in order to lower the levels of these residues absorbed on the surface of the materials to a safe operational value. A typical volume for each batch using this EtO process is 0.2 to 50 cu. ft. within the health and dental care environments.

A number of other approaches for performing sterilization have also been employed. One such process is high pressure steam autoclaving. However, this requires high temperature and is not suitable for materials which are affected by either moisture or high temperature, e.g., corrodable and sharp-edged metals, plastic-made devices, etc., employed by the hospital and the dental communities.

Another approach utilizes either x-rays or radioactive sources. The x-ray approach is difficult and expensive. The use of radioactive sources requires expensive waste disposal procedures, as well as requiring radiation safety precautions. The radiation approach also presents problems because of radiation-induced molecular changes of some materials, which, for example, may render flexible materials brittle, e.g., catheters.

It is therefore a primary object of the present invention to provide a process and apparatus for dry sterilization of medical and dental devices and materials, which can be operated efficiently, both with respect to time and volume and which can be carried out below 70° C.

It is another object of the present invention to provide a safe, nontoxic, process for the sterilization and surface treatment of medical and dental devices and materials, a process which does not employ toxic feed gases and one which does not yield toxic absorbed surface residues and by-products.

SUMMARY OF THE INVENTION

Broadly speaking in the present invention, sterilization or surface treatment is achieved by exposing the medical or dental devices and materials to a highly reducing gas plasma like that generated by gas discharging molecular hydrogen, or to a highly oxidizing gas plasma, for example, one containing oxygen. Depending on the specific sterilization requirements, a mildly oxidizing environment, somewhere between the environment offered by oxygen and that offered by hydrogen is presented by gas discharging molecular nitrogen, either in pure state, or in multicomponent mixtures with hydrogen or oxygen, supplemented by an inert gas. In such a manner, plasma discharge chemical-physical parameters can be adjusted to fit almost any practical application of sterilization and surface treatment.

Such a plasma is generated by creating an electrical discharge in a gaseous atmosphere maintained at subatmospheric or atmospheric pressure, within which the materials to be sterilized are placed.

Generation of gas plasmas is a very well developed discipline, which has been specifically employed in semiconductor processing. See, for example, U.S. Letters Pat. Nos. 3,951,709; 4,028,155; 4,353,777; 4,362,632; 4,505,782 and RE 30,505 assigned to the present inventor.

In one instance the gas plasma sterilization process of this invention involves evacuating a chamber to a relatively low pressure after the devices or materials to be sterilized or treated have been placed within it.

An oxidizing gaseous atmosphere, as an example, is then provided to the chamber at a relatively low pressure, typically in the range 10 microns Hg to 10 torr, corresponding to a continuous gaseous flow rate range of 20 to 3000 standard cc per minute. An electrical discharge is produced within the chamber by conventional means, such as a microwave cavity or a radio frequency (RF) excited electrode. Alternatively, RF power in the power density range 0.0125–0.08 W/cm$^3$ may be coupled into the gas via a single electrode disposed within the chamber in a nonsymmetrical electrical configuration, or via two electrodes contained within the chamber in an electrically symmetrical configuration. In either case the material to be sterilized is placed on one of the electrodes, while the chamber's wall is commonly maintained at ground potential.

The nonsymmetrical arrangement provides the basis for a low plasma potential mode of operation which is conducive to low sterilization temperatures and the suppression of otherwise deleterious ion bombardment and contamination of the devices and materials.

The resultant discharge produces a gas plasma including both excited electrically charged gaseous species and excited electrically neutral gaseous species. For example, free radicals of atomic oxygen as well as excited molecular oxygen are formed in a discharge through molecular oxygen. These oxygen-bearing active species interact chemically with the proteinaceous components of the microorganisms residing on the surfaces of medical or dental devices to be sterilized, thereby denaturing the proteinaceous molecules and achieving kill rates of microorganisms equivalent to a probability of microorganism survival of less than one in a million.

The efficiency of this process is due, in part, to the fact that the gaseous plasma entities are very reactive and atomically small (usually monoatomic or diatomic) and therefore exhibit an enhanced ability to chemically attach themselves to a proteinaceous structure and/or abstract (remove) hydrogen atoms from it. It was also ascertained that the presence of low levels of water vapor in the plasma feed gas enhances sterilization efficiency dramatically. It is believed that accentuation of active species concentration and/or favorable preconditioning of micro-organisms' proteinaceous structure occurs in the presence of moisture during the discharge process. These processes are responsible for the total kill of the microorganisms. The kinetic space (or steric) restriction for this type of interaction is at least one thousand times lower than that for EtO alkylation.

Several specific types of interaction take place. One specific interaction is hydrogen abstraction from amino groups. Another is rupturing ring structures, particularly those including nitrogen, or carbon-carbon bond cleavages. It is important to note that these processes produce only gaseous effluents, such as water vapor and carbon dioxide, which would not remain absorbed on the surface of medical devices, but would, instead, be carried away from such devices with the main gas stream to the pump.

This sterilization process may be used with pre-packaged materials, such as disposable or reusable devices contained within gas-permable bags or pouches. With sealed pouches (e.g., polyethylene/Tyvek packaging), the barrier wall of the package is pervious to the relatively small active species of the sterilizing plasma, but impervious to the larger proteinaceous microorganisms. (Tyvek is a bonded polyolefin produced by DuPont.)

After evacuation of the chamber, and introduction of the gas or gas mixture, the gas(es) will permeate the package wall with a dynamic free exchange of gas(es) from within and from outside the package.

Upon striking a microwave or an RF discharge to form the plasma, are, depending upon electrical configuration and pressure, the plasma may actually be created within and outside the package or, alternatively, the package may be placed in a substantially electrically shielded (field-free) glowless zone, so that it is subject to predominantly electrically neutral, rather than electrically charged, active species which pass through the packaging wall to interact with the surface of the materials it contains.

In yet a different electrical configuration, the packages containing devices to be sterilized can be placed on a conveyor belt and swept into an atmospheric pressure corona discharge gap operated in ambient air. With this configuration, the discharge electrodes are comprised of a grounded metal-backed conveyor belt forming the bottom electrode, while the top electrode is comprised of a metal block with multiple needle-like nozzles for the dispersion of gas into the discharge gap.

Sterilization with this continuous, in-line, apparatus, is brought about by either ozone formation, due to presence of discharged oxygen in air, or due to any other oxidizing gas mixture that can be introduced into the discharge gap via a plurality of nozzles, which are an integral part of the top electrode.

This corona discharge will normally operate in the power density range 5–15 W/cm$^2$ and in the frequency range 10–100 KHz and 13–27 MHz, associated with gas flows in the range of several standard liters per second.

For example, in order to enable: device sterilization by a strongly oxidizing plasma when employing the process with a polyethylene-based packaging, it is necessary to provide that oxygen-bearing active species can permeate through the organic package barrier in the first place, and that a sufficient number of these species traverse that barrier in order to effectively kill all microorganisms on a medical or dental device enclosed within the pouch.

Relevant strongly reducing, oxidizing, mildy oxidizing or mildy reducing conditions can be obtained by plasma discharging diatomic gases like hydrogen, oxygen, nitrogen, halogens, or binary mixtures of oxygen and hydrogen, oxygen and nitrogen (e.g., air), oxygen and inert gases, or the gaseous combination of oxygen, nitrogen and inert gases like helium or argon, depending on the particular substances to be sterilized or treated.

The predominance of oxygen in the above mixtures is preferred but not mandatory. A predominance of nitrogen, for example, will result in mildly oxidizing conditions, but in somewhat higher process temperatures during sterilization for a given reaction pressure and power density. The inert gas fraction can be variable in the range 10 to 95%; the higher the fraction, the lower the processing temperature for a given pressure and power density. However, sterilization exposure time increases the higher the inert gas fraction in the mix. Substitution of argon for helium, for example, will result in higher sterilization temperatures for a given pressure and power density. In this case, instability of the gas discharge operation may set in, requiring a power density increase at a given pressure, compared to that employed with helium, resulting in higher process temperatures.

Effective sterilization can also be obtained with a pure reducing hydrogen plasma or with a plasma discharge through pure inert gases like for example, helium, argon, and their mixtures, due to their very strong hydrogen atom abstraction (removal) capabilities from proteinaceous structures of microorganisms. The addition of pure helium to an argon sterilizing plasma will enhance the stability of the latter and reduce overall sterilization temperatures. Hydrogen and its mixtures with either nitrogen or oxygen, or with both, in the presence or absence of an inert gas, will show effective sterilization capabilities over a wide range of concentrations in these mixtures, thereby enhancing sterilization process flexibility and versatility.

A first objective of facilitating the gaseous permeation through an organic barrier (e.g., plastic or paper) is accomplished by evacuating the chamber (containing the loaded pouches) to a base pressure of approximately 20 microns Hg. This rids the pouches of previously entrapped atmospheric air, and equalizes the pressure inside the pouch to that inside the chamber (across the organic barrier). The subsequent introduction into the chamber of an oxygen-containing gas, in a typical situation, will establish an instantaneous higher pressure inside the chamber (outside the pouch) relative to that inside the pouch. This pressure gradient across the pouches' barrier will serve as the initial driving force of gas into the pouch. At an equilibrated state, an active and ongoing interchange of molecules across the barrier will take place, attempting at all times to maintain the same pressure on both sides of the organic barrier. Upon striking a discharge through this gas, oxygen-bearing active species will be generated. Typically, these active species will be deactivated in large amounts by the organic barrier or due to interaction with neighboring metallic surfaces. This will commonly substantially reduce the availability of these active species to do the sterilizing job.

In order to accomplish the objective of generating a sufficient number of reactive species traversing the organic barrier of a package to effect efficient sterilization cycles, the plasma discharging of gaseous moisture mixtures proved extremely beneficial. plasma discharging of various innocuous gases containing moisture levels in the range 100 to 10,000 ppm of water vapor enabled the accentuation of active species concentration by more than a factor of two, thereby substantially shortening sterilization exposure times. Consequently, in a few system configurations which were previously characterized by relatively high processing temperatures, process temperatures were now kept sufficiently low due to the shortened sterilization cycles. Effective binary moisture mixtures were those comprised of oxygen, nitrogen, hydrogen and argon. Ternary moisture mixtures of nitrogen-oxygen and argon - oxygen were somewhat more effective at similar power densities than moisture mixtures of pure nitrogen or pure argon. Moisture mixtures containing halogens although very effective, were too corrosive and toxic. The most effective moisture mixture was that of oxygen, reducing sterilization cycles by more than a factor of two.

In addition, it was found that the organic barrier of a packaging pouch could be passivated in such a way as to substantially reduce its take-up of oxygen-bearing active species needed as a sterilizing agent and one which must render a final non-toxic medical device, without the formation of any toxic by-products.

One such passivation method consists of simultaneously introducing into the chamber a gaseous mixture, which in addition to oxygen-containing gas(es), also contains selected other gases as set forth below:

1. Organohalogens, based on carbon and/or silicon, attached to any of the known halogens. Particularly those organic compounds of carbon and/or silicon that are saturated or unsaturated and contain in their molecular structures one (1) or two (2) carbon or silicon atoms attached to: a predominance of fluorine atoms; a predominance of chlorine atoms; a predominance of bromine or iodine atoms; an equal number of fluorine and chlorine atoms simultaneously; an equal number of chlorine and bromine atoms simultaneously; an equal number of fluorine and bromine atoms simultaneously; an equal number of fluorine and iodine atoms simultaneously an equal number of chlorine and iodine atoms simultaneously. A predominance of fluorine in these compounds includes structures where all other atoms attached to a carbon or a silicon atom can be all the other halogens, or only one or two other halogens out of the four halogens known, in conjunction with other atoms, as for example hydrogen. The same comments apply to a predominance of chlorine, bromine and iodine. For the latter, however, the simultaneous presence of bromine is unlikely to be practical due to a low volatility of the structure, but the simultaneous presence of fluorine or chlorine, or both, is practical. It is worth noting that hydrogen-containing organohalogens will have a tendency to polymerize under plasma conditions, and in some cases, be flammable in as-received condition.

Most effective sterilizing mixtures of oxygen and an organohalogen are those where the organohalogen is a mixture of organohalogens in itself, either based on carbon and/or silicon, where the oxygen fraction is over 70% by volume; yet sterilization will be effected for lower oxygen content at the expense of excessive halogenation of the surface of the material to be sterilized, and at the expense of excessive loss of transparency of the wrapping pouch.

2. Organohalogens in conjunction with either nitrogen or an inert gas like helium or argon. In these cases, it is considered practical to keep the fraction of the inert gas in predominance in order to keep the process temperature as low as possible. Inert gas fractions up to 95% by volume will be effective in killing microorganisms. The nitrogen fraction is ideally kept below that of the oxygen fraction.

3. Inorganic halogens, defined as compounds not containing carbon or silicon, but preferably containing as the central atom or atoms either hydrogen, nitrogen, sulfur, boron, or phosphorus linked to any of the known halogens in a similar manner as described for the organohalogens under item 1 above, or defined as compounds that contain only halogens without a different central atom, like for example molecular halogens (e.g., $F_2$, $Cl_2$) and the interhalogens which contain two dissimilar halogen atoms (e.g., Cl-F, I-F, Br-Cl based compounds, etc.). Also in this case the inorganic halogen maybe, in itself, a mixture of different inorganic halogens as defined above.

Most effective sterilizing mixtures of oxygen and an inorganic halogen are those where the oxygen fraction is over 80% by volume; yet sterilization will be effected for lower oxygen content at the expense of excessive halogenation of the surface of the material to be sterilized, and at the expense of excessive loss of transparency of the wrapping pouch.

4. Inorganic halogens in conjunction with either nitrogen or an inert gas as described in item 2 above.

5. Inorganic oxyhalogenated compounds, not containing carbon or silicon, but preferably contain either nitrogen, phosphorus, or sulfur, each of which is simultaneously attached to oxygen and a halogen (e.g., NOCl, SOCl$_2$, POCl$_3$, etc.). More specifically, the nitrogen-oxygen, or the sulfur-oxygen, or the phosphorus-oxygen entities in the previous examples are linked to any of the known halogens in a similar manner as described for the organohalogens under item 1 above. The inorganic oxyhalogenated fraction may be, in itself, a mixture of different inorganic oxyhalogenated compounds as defined above.

Most effective sterilizing mixtures of oxygen and an inorganic oxyhalogenated structure are those where the oxygen fraction is over 70% by volume; yet effective sterilization will be obtained for lower oxygen content at the expense of excessive halogenation of the surface to be sterilized, and at the expense of excessive loss of transparency of the wrapping pouch.

6. Inorganic oxyhalogenated compounds in conjunction with free nitrogen or an inert gas as described in item 2 above.

7. Multicomponent mixtures comprised of members in each of the aforementioned groups. The simultaneous presence of free nitrogen and an inert gas like helium or argon in any of the above mentioned groups, or in multicomponent mixtures comprised of members in each of the aforementioned groups, will also be effective in killing microorganisms. The free nitrogen fraction should be ideally below that of oxygen in order to maintain a lower reaction temperature.

More specific and relatively simple multicomponent mixtures that are effective sterilants as well as effective organic barrier passivation agents are listed below:

| Specific Multicomponent Mixtures Comprised of Fractions A + B (percent of fraction is by volume) | |
|---|---|
| Fraction A | Fraction B |
| O$_2$(92–97%) | CF$_4$(3–8%) |
| [O$_2$(40%)—He(60%)] | CF$_4$(0.25–3%) |
| [O$_2$(8%)—CF$_4$(92%)] | He(80%) |
| [O$_2$(17%)—CF$_4$(83%)] | He(80%) |
| [O$_2$(83%)—CF$_4$(17%)] | He(80%) |
| [O$_2$(92%)—CF$_4$(8%)] | He(80%) |

Many of the aforementioned gas mixtures are, in themselves, novel chemical compositions.

The plasma discharge through such a composite mixture will, for example, create both oxygen-bearing and fluorine, or chlorine-bearing active species simultaneously. The latter will predominantly be responsible for passivating the organic barrier, since fluorination or chlorination, rather than oxidation of the organic barrier is favored thermodynamically. Therefore the take-up of fluorine or chlorine-bearing active species by the organic barrier of the pouch will be preferential. This will leave a relatively larger fraction of oxygen-bearing active species available for sterilization, since the latter cannot easily be taken up by a fluorinated or chlorinated surface.

In addition, sterilization by oxygen-bearing active species may be aided, for example, by simultaneously discharging an oxygen-containing and fluorine or chlorine containing gas residing inside the enclosing pouch. This gas had previously permeated through the organic barrier prior to the commencement of the discharge. This will create active species that contain both oxygen and fluorine or chlorine within the pouch directly. As previously described, the competition for take-up by the organic barrier (pouch) will be won by the fluorinating or chlorinating species, leaving a larger net concentration of active species containing oxygen to do an effective sterilizing job.

However, residual fluorine or chlorine-bearing active species within the pouch and not taken-up by it will also perform effective surface sterilization, since they are strongly chemically oxidizing agents. But, the fraction of fluorine or chlorine-containing gas in the original composite gaseous mixture, is substantially smaller than the oxygen-containing component. Thus, a major portion of microorganisms kill will be attributed to the oxygen-bearing species in the plasma. In either case, however, the end result is a continuous attack on the proteinaceous structure of the microorganism resulting in its degradation and fragmentation into gaseous products. This chemical action by the reactive plasma is to initially modify (denature) the proteinaceous network of the microorganism, disrupting its metabolism at a minimum, but more commonly impeding its reproduction.

DESCRIPTION OF PREFERRED EMBODIMENTS

Figure 1:
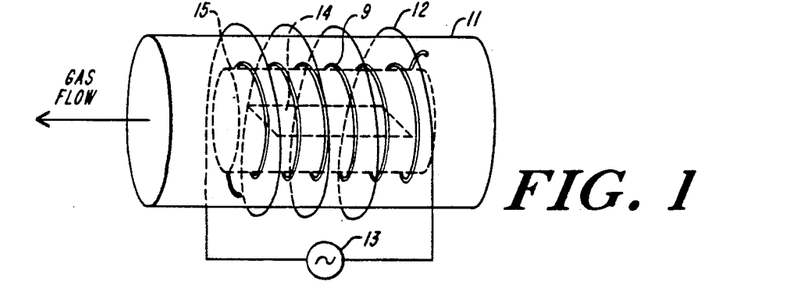
FIG. 1 is a general diagrammatic illustration of an apparatus suitable for use in the practice of this invention.

FIG. 1 is a general diagrammatic illustration of an RF excited discharge chamber of the type used in the process of this invention. The cylindrical chamber 11 is formed, in this instance, of glass or quartz and encloses within it the material 14 to be treated. The chamber is commonly connected to a mechanical vacuum pump (not shown) that establishes sub-atmospheric pressure conditions within the chamber. An exciter coil 12 couples RF energy from RF source 13 to the gas enclosed within the gas tight chamber creating a plasma therein.

Alternatively, a microwave discharge cavity operating at 2450 MHz may replace the RF exciter coil to couple power into the gas. With a suitable selection of a reducing gas, like hydrogen, or an oxidizing gas, such as oxygen, as a typical example, a discharge may be initiated and maintained within the chamber. In the gas plasma formed by such a discharge a number of excited species, both molecular and atomic, are formed. The interaction of these species with a surface of the device or material to be sterilized accomplishes the sterilization in the manner described above. The time duration of the process needed to achieve satisfactory sterilization will vary with other parameters of the discharge such as gas flow, pressure, RF or microwave power density, and load size.

Figure 2:
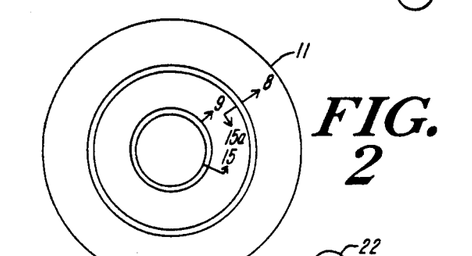
FIG. 2 is a cross sectional view of another apparatus suitable for use in the practice of this invention.

In the embodiment illustrated in FIG. 1 the apparatus includes an inner perforated metallic cylinder 15 mounted generally concentric with the long axis of the chamber 11, to form within the perforated cylinder a substantially glowless, field-free zone. The perforated cylinder 15 is electrically-floating and is cooled by recirculating a suitable coolant (e.g., a 50—50 mixture of water and ethylene glycol) through cooling coils 9 wrapped around the cylinder's length, to effect low sterilization temperatures (<70° C.) Still lower sterilization temperatures could be effected with two concentric perforated metallic cylinders 15 and 15a, surrounded by cooling coils 9 and 8, respectively, and enclosed by non-conducting chamber 11, as shown in FIG. 2. Energy coupling into this chamber is accomplished in a similar manner as described in FIG. 1. In a few cases, the configurations described in FIGS. 1 and 2 may not require cooling coils 8 and 9 if the plasma feed gas contains low levels of water vapor for the enhancement of sterilization efficiency and the reduction of processing cycle time and temperature.

The resultant glowless and field-free zone within the confines of the electrically-floating perforated cylinders could be ascribed to electrical faraday-cage effects, coupled with catalytic deactivation of active species, which are the precursors of visible emission, on the metallic surface of the perforated cylinder.

Figure 3:
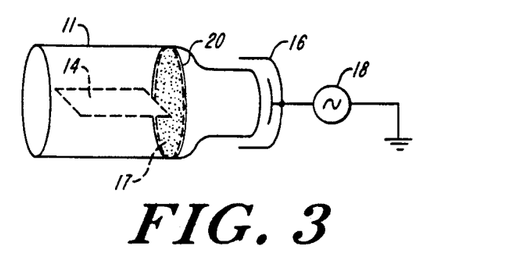
FIG. 3 is a generally diagrammatic illustration of another apparatus suitable for use in the practice of this invention.

When, as illustrated in FIG. 3, a microwave energy source 18 at for example, 2540 MHz. is employed in lieu of the RF generator 13, the perforated metallic cylinder cannot be mounted concentric about the long axis of the chamber. Instead, the microwave cavity 16 is mounted at one end of a metallic or non-metallic chamber 11, and a perforated metallic shield 17 cooled by coolant-recirculating coils 20 may be placed just beyond it toward the opposite end of the chamber, spanning the entire diameter cross section of the chamber, thus creating a field-free and glowless reactive zone immediately below it and away from the microwave cavity. These arrangements permit material 14 placed within this zone to be generally isolated from electrically charged species, while allowing the electrically neutral reactive plasma species, such as for example, oxygen radicals, to interact with the surface of the material to be sterilized. In this manner, sterilization is commonly effected at substantially lower process temperatures.

Alternatively, the perforated metallic shield 17 may be removed, if microwave cavity 16 is remotely located from material 14.

Microwave discharges lend themselves to this mode of operation, since the effectiveness of neutral active species generated in such a discharge survive substantial distances downstream, and away from, the microwave cavity itself. This is a direct consequence of the higher population of electrons in microwave plasmas, and consequently the higher degree of ionization and dissociation in these discharges. Also, microwave plasma electric probe measurements indicated plasma potentials nearly equal to ground potential, thereby practically eliminating energic particle bombardment during processing. This mode of operation is thus well suited for low temperature exposure of heat - sensitive devices and material, even for extended periods of sterilization time.

In the most preferred embodiments, the chamber is formed of a metallic electrically grounded and water-cooled outer shell with either a single internal perforated cylindrical shield, as shown in FIG. 1, or perhaps with two such metallic shields, as shown in FIG. 2, which may be also purposely cooled, the RF energy being coupled, in this latter configuration, between the two conducting perforated cylinders. In either case, conditions for low plasma potentials will prevail, with the discharge glow being confined to the space between the inner wall of the chamber and the surface(s) of the perforated cylinder(s), leaving the work volume defined by the inner perforated cylinder substantially field-free, void of the plasma glow, and at a relatively low operating temperature.

Figure 4:
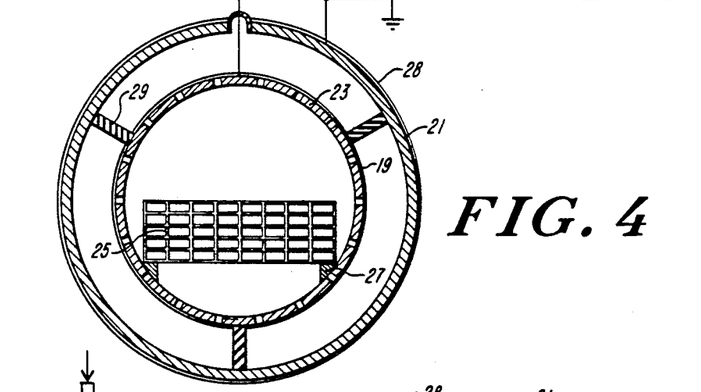
FIG. 4 is a cross sectional view of another embodiment of a sterilization chamber for use in the practice of the invention.
Figure 5:
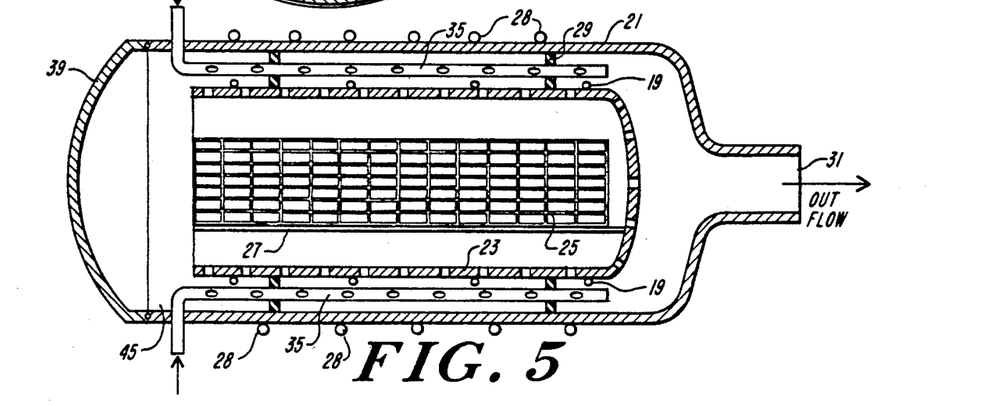
FIG. 5 is a side view of the apparatus of FIG. 4.

One such chamber configuration is illustrated in FIGS. 4 and 5. The cylindrical outer wall 21, typically formed of aluminum or stainless steel, is maintained at ground potential and serves as the chamber enclosure. This enclosure may be water-cooled with the aid of cooling coils 28 wrapped around it. Suitable dimensions for this chamber are a diameter of 36" and a length of 48". A metallic perforated inner cylinder 23 cooled by cooling coils 19 is mounted on insulating spacers 29 within the chamber so that it is positioned generally parallel with the long axis of the outer wall 21 of the chamber and concentric with it. These spacers may be formed of any suitable non-reactive and insulating type of material such as ceramic. The cylinder perforations are typically 2.5-4 mm diameter holes spaced in all directions from one another by approximately 0.5 cm in a triangulated manner. Longitudinal support rails 27 are fastened to the inner wall of the perforated cylinder 23 to support a wire basket 25 in which the materials and devices to be sterilized are placed. A suitable RF source 22 is coupled between the grounded outer chamber wall 21 and the perforated inner cylinder 23. Usually this RF source should be capable of producing an RF output in the range 0.01 to 0.1 W/cm$^3$ at frequencies in the 10-100 kilohertz or 13-27 megahertz range.

As illustrated in FIG. 5, an evacuation port 31 at the end of cylinder 21 is connected to a pump (not shown) and provides for suitable evacuation of the chamber and for continuous gas flow during the sterilization process. The gas supplied for the discharge is generally flowed through the chamber by means of perforated diffusion tubes 35. Alternately, gas may be introduced into the chamber via a gas dispersion device (not shown) mounted behind chamber door 39 from the inside.

Material to be sterilized may be placed within wire basket 25 resting on rail 27 through the entry port behind chamber door 39. Chamber door 39 may be any suitable closure that can be conveniently opened and closed and left in a sealed position during evacuation and the gas discharge operation.

Figure 6:
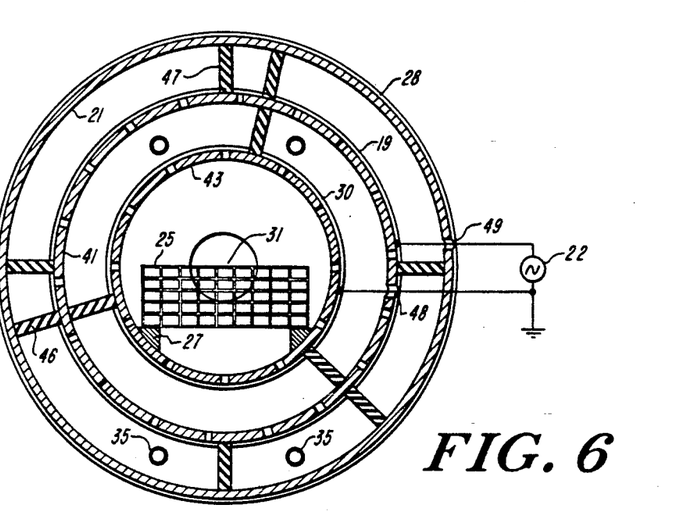
FIGS. 6, 7, 8, 9, 10, 11, 12, 13 and 14 are cross sectional and side views of alternative embodiments.

FIG. 6 illustrates a second preferred embodiment of the apparatus for practicing the process of the invention. In this configuration, the outer chamber wall 21 may be water-cooled by cooling coils 28, is again formed of metal, such as electrically grounded aluminum or stainless steel, and is of similar dimensions to that illustrated in FIG. 4. Mounted within the chamber is an inner concentric cylinder 43 formed of a perforated metal which may be purposely cooled by cooling coils 30, and is supported on insulating support struts 46. The spacing between the inner wall of the chamber and the perforated interior cylinder may range typically from 10 to 17 cm, where the chamber has an I.D. of 36". A second metallic perforated cylinder 41 is concentrically mounted intermediate between the inner perforated cylinder 43 and the inner wall of the chamber and may also be cooled by cooling coils 19. This second perforated cylinder is supported on insulating struts 47 and is spaced typically 4 to 7 cm away from the inner perforated cylinder 43. The insulator struts may again be formed of a ceramic material. Mounted on the interior of the inner concentric cylinder 43 are support rails 27 for carrying a wire basket which would contain the materials to be sterilized. Both the outer chamber wall 21 and the inner perforated cylinder 43 are electrically connected to point of potential reference (ground). Electrical connections would most usually be made through ceramic seal feedthroughs 48 and 49. The intermediate cylinder 41 is electrically connected to one side of the RF power supply 22, the other side of which is connected to the point of potential reference.

While a variety of conventional RF sources may be used, the most typical value for the RF frequency is 13.56 MHz or, alternatively, 10-100 KHz. As in the embodiment of FIG. 5 longitudinally extending gas diffusion tubes 35 may be employed to provide the gas to the interior of the chamber. Typically each tube would have holes of diameter between 0.5 and 1.5 mm, spaced approximately 1" apart along its length. The hole diameters closer to the gas source would be of the smaller diameter. Alternatively, gas inlets may be provided behind chamber door 39. As indicated in the embodiments of FIGS. 4, 5 and 6 the perforated inner cylinders may be open-ended at both ends or, may be closed with the same perforated stock as is used to form the cylinder(s). The sterilization chambers shown in FIGS. 4, 5 and 6 may be connected to a microwave discharge source, typically operating at 2540 MHz, in lieu of an RF energy source. In this case, the concentric perforated metallic cylinder(s) may be replaced by a single perforated shield in accordance with the operational description given for FIG. 3.

Figure 7:
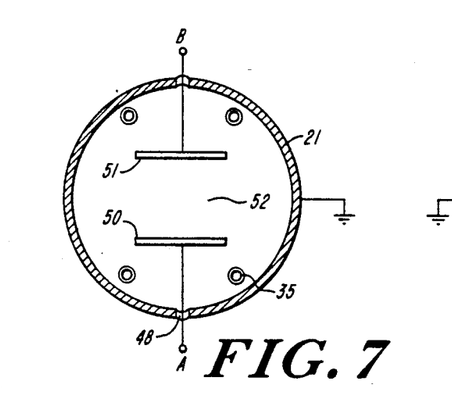

FIG. 7 illustrates a third preferred embodiment of the apparatus for practicing the process of the invention. In this diagrammatic description the outer chamber wall 21 is again formed of metal, such as aluminum or stainless steel, and is of similar dimensions to that illustrated in FIG. 4. Mounted within the chamber are two planar, metallic, electrodes 50 and 51, preferably constructed of aluminum which may be coated with insulating aluminum oxide. The gap 52 between electrodes 50 and 51, is adjustable by virtue of the movable bottom electrode 50. Terminals A and B are connected to the electrodes via an insulating feedthrough 48. The outer end of these terminals may be connected to an RF source (not shown) in such a way that when terminal B is connected to a ground potential, terminal A must be connected to the RF source, or vice versa, providing for an electrical symmetrical configuration. The work load to be sterilized is placed on lower electrode 50.

It is important to maintain the distance between the electrodes always smaller than the distance of the RF-powered electrode's edge to the grounded chamber's wall. This enables a well defined and intense plasma glow to be confined to space 52 between the electrodes and prevents deleterious sparking. The electrode material may also be made of the perforated stock previously mentioned. However, it is desirable to have the RF-powered electrode made of solid stock to enable very efficient water-cooling of that electrode. The bottom electrode may also be made of solid stock to enable a cooler surface upon which the work load to be sterilized will be placed. This chamber will commonly be evacuated to 10-100 microns Hg before gas introduction via the perforated gas diffusion tubes 35. practical device sterilization can be obtained with process parameters for gas flow rates in the range 20 to 3000 scc/m, corresponding to a total sterilization reaction pressure of 10-5000 microns Hg, at a range of RF power densities of 0.0125 to 0.08 W/cm$^3$. Process exposure times will depend on load size and are commonly in the range 2 to 120 min.

Figure 8:
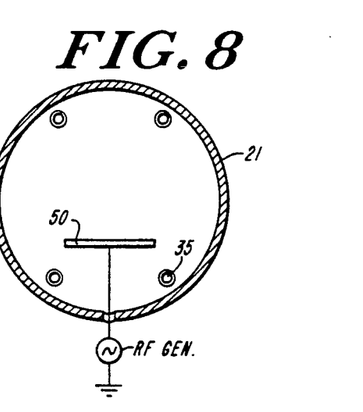

FIG. 8 illustrates in diagrammatic form yet another preferred embodiment for practicing the process of the invention. The outer wall of chamber 21 is again formed of metal, such as aluminum or stainless steel maintained at ground potential, and is of similar dimensions to that illustrated in FIG. 4. Mounted within the chamber is a single planar, metallic, electrode 50, preferably constructed of aluminum which may be coated with insulating aluminum oxide to reduce RF sputtering. This electrode is commonly connected to an RF source in the MHz range and carries the work load to be sterilized. This electrode has commonly a total surface area which is at least four times smaller than the total internal surface area of the grounded chamber, to effect a low plasma potential mode of operation. This arrangement, coupled with low power densities (see below) is conducive to very low sterilization temperatures.

This electrical configuration is usually referred to as asymmetric and is conducive to generating an extremely uniform plasma glow filling the entire volume of the processing chamber. It is also responsible for the development of a characteristic accelerating potential at the surface of electrode 50, associated with a thin "dark space" through which positive plasma ions will accelerate and impinge on the electrode and the work load it normally carries.

This arrangement is recommended for hard-to-sterilize materials almost exclusively, particularly for Sterilization of metallic devices replete with a high density of cracks and crevices.

The main advantage of this process chamber configuration is its ability to render efficient sterilization at relatively low power densities in the range of 0.0125-0.025 W/cm$^3$. This configuration is also easily scalable as a function of work load size.

This process chamber commonly operates with at least an order of magnitude lower pressure than the pressure for chambers described in FIGS. 1 through 7, while the gas dispersion tubes 35 are similar in construction to those previously mentioned. To prevent RF sputtering of electrode 50 due to positive ion bombardment, it may either be hard-anodized or alternatively aluminum oxide spray-coated.

Figure 9:
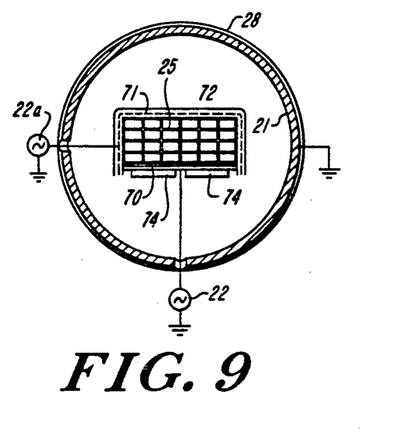

One particular sub-configuration to that described in FIG. 8 is illustrated in FIG. 9. In this configuration chamber 21 is water-cooled by cooling coils 28 and contains a perforated metallic enclosure 71 totally surrounding and containing electrode 70. This enclosure may be cooled by coolant-recirculating coils 72 and may be connected to a separate RF source 22a, of a different frequency than that of source 22. This perforated enclosure may be equipped with an open/close hinging mechanism (not shown) to enable access for material to be sterilized to be placed on electrode 70 contained within enclosure 71. This yields the beneficial effect of being able to separately control the abundance of sterilizing active species and their impinging energy. RF power applied to electrode 70, which may or may not include a negative DC potential from a separate DC supply, (not shown), will control energy of ion impingement, while RF power applied to the auxiliary perforated enclosure 71, will control active species abundance.

With this configuration, RF power sources operating at 100 KHz and 13.56 MHz may be used in the various possible permutations. Interesting results are obtained by mixing both frequencies while being applied to a single element. Commonly, one frequency has to be applied at a higher power fraction, usually around 90% of the total applied power to the same element. Such interesting process results were obtained when the two different frequencies were mixed and applied to electrode 70 in the absence of any auxiliary perforated enclosure. The mixed frequency concept also lends itself to low power density sterilization in the range 0.0125 to 0.025 W/cm$^3$, with the advantage of maintaining the overall temperature relatively low (below 50° C.), particularly when electrode 70 is water-cooled by cooling coils 74.

It is worth noting that the auxiliary perforated enclosure 71 ought to be of high mesh transparency to allow the plasma glow to extend past it and contact electrode 70. Best operating conditions will be obtained for the smallest surface area of this perforated metallic enclosure. In a few instances, this metallic enclosure was connected to ground, yielding effective sterilization data.

Figure 10:
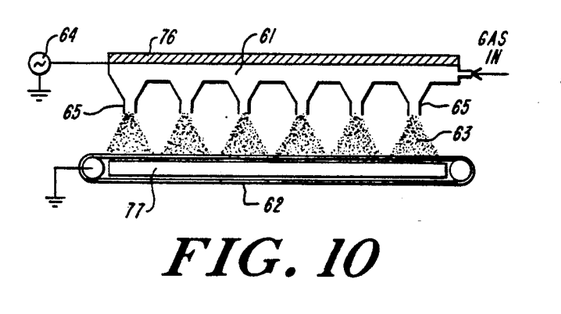

FIG. 10 illustrates diagrammatically a preferred embodiment for practicing the process of the invention under atmospheric pressure conditions in ambient air. In this configuration no vacuum capability is required. Material to be sterilized is placed on grounded and water-cooled conveyor belt 62 which sweeps the load across the discharge gap created between conveyor belt 62 and RF-powered and water-cooled electrode 61. Electrode 61 cooled by cooling coil 76 produces a large plurality of needle-like discharges which create individual discharge sparks toward the counter grounded electrode 62. The larger the gap between the electrodes, the higher the power needed to initiate the discharge in air.

Sterilization is effected due to ozone formation following the discharge of oxygen in the ambient air. Power density requirements in the range 5 to 15 W/cm$^2$ are not uncommon. Maintaining a controlled relative humidity of 50 to 60% in the discharge gap will facilitate initiation of the discharge and promote atomic oxygen generation. The latter serves as a precursor to ozone formation, the final desired sterilant in this configuration.

Ozone toxicity inhibits wide acceptance of such a corona discharge in air for the purpose of medical or dental device sterilization. Alternatively, therefore, the RF-powered electrode 61 may assume a configuration comprised of multiple open nozzles 65, capable of dispersing oxidizing gases immediately adjacent to conveyor belt 62. In this configuration the discharge would still be created in ambient air, however the dispersion through the open-nozzles 65 of a judiciously selected feed gas will increase the local concentration of its active species 63 relative to that of ozone. In this manner, sterilization would be attributable to active species derived from any feed gas introduced into the hollow RF-powered electrode 61 and not to the deleterious ozone gas.

The dispersing nozzles 65 may assume different configurations. For example, separate nozzle tubes may be inserted into a hollow section of electrode block 61, which may or may not be of different material than electrode block 61. These tubes may also be screwed into the electrode block 61 for easy replacement. A typical hole size for each individual nozzle is in the range 0.015–0.040''.

The advantages of this discharge configuration are mainly in terms of system simplicity and in the context of continuous operation, coupled with the ability to easily change the residence time of a work load within the discharge gap.

Disadvantages are commonly associated with erosion and degradation of both electrodes 61 and 62. Electrode 61 should be constructed from oxidation-resistant materials (e.g., tungsten, molybdenum or alloys thereof). The grounded conveyor belt electrode 62 may be constructed from stainless steel or any other suitable nickel-coated metal, and may be cooled by cooling coil 77. Alternatively, a dielectric conveyor belt may be used. With such an arrangement, the insulating belt is mounted in close proximity to a stationery grounded and fluid cooled metallic block serving as the counter electrode. The conveyor belt ought to be resistant to electrical punch-through and be constructed from fluorinated, fluorinated/chlorinated or fluorinated/-chlorinated nitrogen-containing hydrocarbons (e.g., DuPont Products). High melting polyimides or Kalrez-like synthetics may serve as alternate construction materials for the conveyor belt. Kalrez is a polyimide manufactured by DuPont.

Other configurations are illustrated in FIGS. 11, 12, 13 and 14. These configurations are preferred embodiments for practicing the process of the invention with narrow bore and elongated tubulation, almost exclusively. They are particularly designated for the treatment and sterilization of fiber optics-based tubulations as, for example, endoscopes, proctoscopes, angioscopes or bronchioscopes, having internal diameters as small as 2 mm and an overall length of about 1000 mm.

The outer wall of elongated chamber 91 is made preferentially of non-metallic material (e.g., glass, ceramic) but, may also be comprised of a metallic/non-metallic structure. The chamber has a minimum internal diameter of one and one half times that of the outside diameter of elongated tubulation 94. The inner and outer surfaces of narrow bore tubulation 94 need to be treated or sterilized. Both ends of narrow and elongated chamber 91 are hermetically plugged with gas permeable but microorganism-impervious membranes 99 (e.g., Tyvek). This arrangement ensures the dynamic flow of an active plasma through and over tubulation 94, and also secures its aseptic condition after sterilization and during prolonged storage.

To effect sterilization or treatment of the inner and outer surfaces of tubulation 94, it is inserted into chamber 91 either bare or sealed within a gas permeable elongated pouch. The chamber is then plugged at both ends with membranes 99.

The chamber is subsequently inserted into exciter coil 92 (FIG. 11) whose terminals are connected to a suitable RF energy source like the one described with respect to FIG. 1.

In another arrangement, the chamber may be inserted within the air gap of capacitive plates 93 (FIG. 12) whose terminals are connected to a suitable RF energy source like the one described with respect to FIG. 1.

Alternatively, chamber 91 may be brought into close proximity to microwave cavity 16 (FIG. 13) whose terminal is connected to a suitable microwave energy source as described with reference to FIG. 3.

Figure 11:
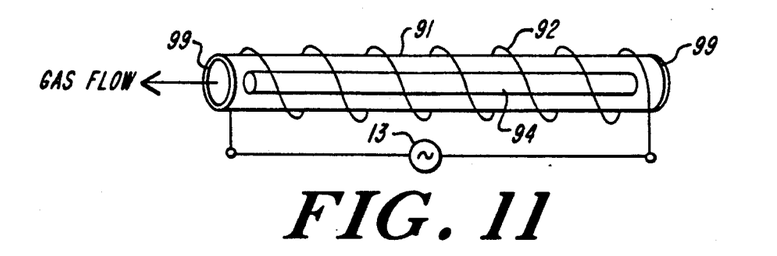
Figure 12:
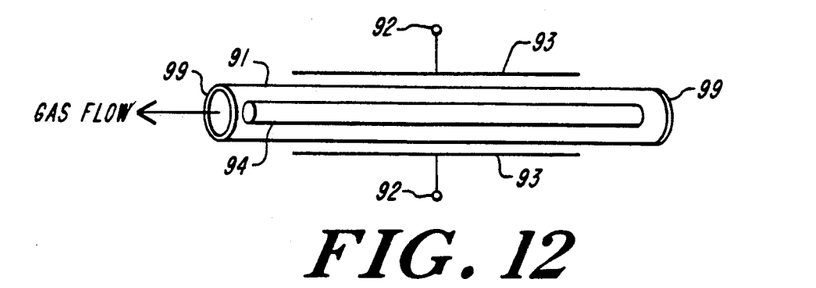
Figure 13:
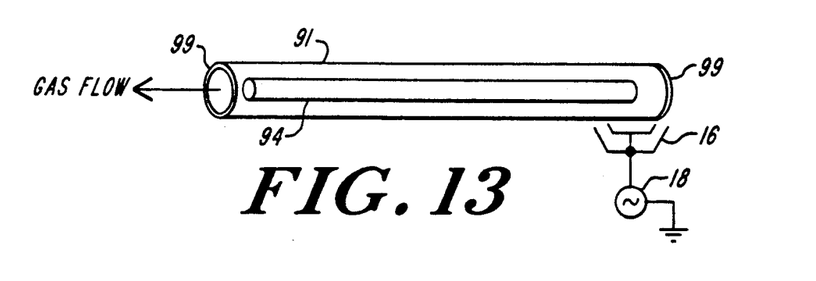

In cases where the chamber is a metallic-non-metallic structure, the various energy sources described in FIGS. 11, 12 and 13 are coupled to the chamber via the non-metallic portion of the chamber.

In each of the configurations of FIGS. 11, 12 and 13, one end of elongated chamber 91 is temporarily vacuum-flanged to a gas delivery and monitoring system (not shown), while the other free end of the chamber is temporarily vacuum-flanged to a gas exhaust pumping system (not shown).

At the end of the sterilization or treatment cycle, the gas flow and the energy source are turned off, chamber 91 is disengaged from the power source and from both vacuum flanges and stored for future use of narrow bore tubulation 94.

For practical reasons, a plurality of chambers 91 may be employed in a parallel electrical arrangement simultaneously, either in an RF or microwave discharge hook-up.

Figure 14:
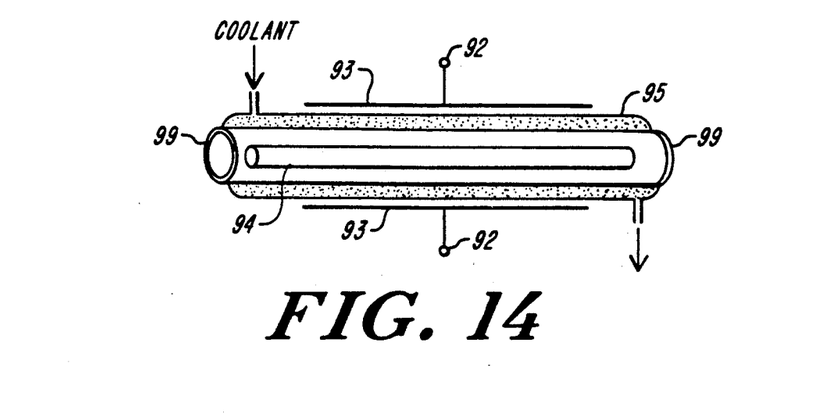

Chamber 91 may have a cooling jacket 95 around it as, for example, shown in FIG. 14. It is not mandatory that exciter coil 92 (FIG. 11) or capacitive plates 93 (FIG. 12) enclose or extend over the entire length of tubulation 94; the latter may be partially contained or not contained at all within coil 92 or capacitor plates 93.

Set forth below are specific examples of suitable operating parameters for effective sterilization employing various apparatus as illustrated in the figures. The particular chamber and corresponding configuration, are referenced in the examples. However, for each of the examples the general technique involved was one in which the material to be sterilized was placed directly in the reaction chamber, or placed within a Tyvek/polyethylene pouch which itself was sealed and placed in a wire basket within the reaction chamber.

The materials used for verification of sterilization effectiveness were "Attest" vials obtained from 3M Company, or "Spordex" bacterial test strips obtained from the American Sterilizer Company, each vial or "Spordex" envelope contained a bacterial strip having an original spore population of not less than $1 \times 10^6$ *Bacillus Subtilis* var Niger per strip, but more commonly in the range $2.2-4.0 \times 10^6$ spores strip. The strips contained the permeable plastic vials were not brought into contact with the culture solution contained in any of the vials prior to sterilization. The vials were placed within the Tyvek/polyethylene bags during the plasma sterilization, alongside devices or instruments to be sterilized. The bags were always sealed during the sterilization process.

For each example the chamber was first evacuated to an initial low pressure level after the materials (in the bags or pouches) were placed within it. The chamber was thereafter filled with the appropriate gas prior to striking the discharge, and the gas continued to flow through the chamber at a controlled rate to establish a steady state sterilization pressure. The discharge was initiated by the application of RF or microwave power as indicated. The discharge was maintained for a controlled time period at the end of which the power was turned off, the chamber was first evacuated, then back-filled with air through a bacteria retentive filter, and later opened and the samples removed. The temperature within the chamber during the process was maintained at less than 70° C., and more typically around 25° C. to 65° C., as sensed by an iron-constantan, type "J", thermocouple circuitry and monitored by an analog temperature meter.

Subsequent to the tests, the spore strips in the "Attest" vials where brought into contact with the self-contained culture solution and incubated for 72 hr, at the end of which period microorganism growth or no growth would be indicated by the resultant color of the culture solution. Alternatively, the spore strips were submitted to an independent testing laboratory which performed a total plate count on the sample strips using a procedure in which 100 milliliters of sterile deionized water were added to each strip in a sterile whirl-pak bag. The bag was then placed in a lab blender for 10 minutes. One 10 milliliter aliquot of sample, a duplicate one milliliter sample, and two consecutive $10^{-1}$ dilutions were plated using Tryptic Soy Agar. The plates were then incubated at 30°-35° C. for 72 hours. After incubation, the plates were read and recorded, and the results calculated on a Colony Forming Unit (CFU) basis.

EXAMPLE 1

With metal chamber and internal uncooled perforated cylinder, (FIG. 4)
Gas: $O_2$(Pure)
Flowrate: 20 scc/min
Pressure: 0.30 torr
Power Density: 0.050 W/cm$^3$
Exposure time: 60 min.
Temperature : 66° C.
Resultant microbial count: <10 CFU (below sensitivity limit of counting technique)
Percent kill: 99.9999%
Metal chamber dimensions: 8"D×8"L

EXAMPLE 2

With metal chamber and internal cooled Perforated cylinder, (FIG. 4)
Gas $O_2$(Pure)
Flowrate: 20 scc/min
Pressure: 0.30 torr
Power Density: 0.050 W/cm$^3$
Exposure time: 60 min.
Temperature : 32° C.
Percent kill: Total kill
Metal chamber dimensions: 8"D×8"L

EXAMPLE 3

With Pyrex chamber and internal cooled perforated cylinder, (FIG. 1)
Gas: $O_2/CF_4$ (8%)
Flowrate: 36 scc/min
Pressure: 0.35 torr
Power Density: 0.050 W/cm$^3$
Exposure time: 60 min.
Temperature: 34° C.
Resultant microbial count: <10 CFU (below the sensitivity limit of counting technique)
Percent kill: 99.9999%
Pyrex chamber dimensions: 8"D×8"L

EXAMPLE 4

With metal chamber and two uncooled internal Perforated cylinders, (FIG. 6)
Gas: $O_2$
Flowrate: 20 scc/min
Pressure: 0.30 torr
Power Density: 0.050 W/cm$^3$
Temperature: 76° C.
Percent kill: Total kill
Metal chamber dimensions: 8"D×8"L

EXAMPLE 5

With metal chamber and two cooled internal perforated cylinders, (FIG. 6)
Gas: $O_2$ Flowrate: 20 scc/min
Pressure: 0.30 torr
Power Density: 0.050 W/cm$^3$
Exposure time: 60 min.
Temperature: 36° C.
Resultant microbial count: <10 CFU
Percent kill: 99.9999%
Metal chamber dimensions: 8"D×8"L

EXAMPLE 6

With Pyrex chamber and cooled internal cylinder, (FIG. 1)
Gas: He(59.85%)—O$_2$(39.90%)-CF$_4$(0.25%)
Flowrate: 48 scc/min
Pressure: 0.35 torr
Power Density: 0.050 W/cm$^3$
Exposure time: 60 min.
Temperature: 31° C.
Resultant microbial count: <10 CFU
Percent kill: 99.9999%
Pyrex chamber dimensions: 8"D×8"L

EXAMPLE 7

With metal chamber and two cooled internal perforated cylinders, (FIG. 6)
Gas: O$_2$(60%)—He(40%)
Flowrate: (total) 42 scc/min
Pressure: 0.35 torr
Power Density: 0.050 W/cm$^3$
Exposure time: 60 min.
Temperature: 32° C.
Resultant microbial count: <10 CFU
Percent kill: 99.9999%
Metal chamber dimensions: 8"D×8"L

EXAMPLE 8

With Pyrex chamber and cooled internal Perforated cylinder, (FIG. 1)
Gas: O$_2$ (pure)
Flowrate: 25 scc/min
Pressure: 0.30 torr
Power Density: 0.015 W/cm$^3$
Exposure time: 30 min.
Temperature: 26° C.
Percent kill: Total kill
Pyrex chamber dimensions: 8"D×8"L
With Pyrex chamber and uncooled internal Perforated cylinder, (FIG. 1)
Gas: O$_2$ (pure)
Flowrate: 25 scc/min
Pressure: 0.30 torr
Power Density: 0.015 W/cm$^3$
Exposure time: 30 min.
Temperature: 83° C.
Percent kill: Total kill
Pyrex chamber dimensions: 8"D×8"L
For the following examples spore population was 4×10$^6$ spores/strip.

EXAMPLE 10

With microwave discharge and internal perforated metallic shield disc, (FIG. 3)
Gas: Helium/Argon (50%/50%, v/v)
Flowrate (total): 80 scc/min
Pressure: 0.40 torr
Power Density: 0.015 W/cm$^3$
Exposure Time: 90 min
Temperature: 29° C.
Resultant Microbial Count: 1.7×10$^2$ CFUs
Percent Kill 99.9993
Pyrex chamber dimensions: 6"D×10"L

EXAMPLE 11

With microwave discharge and internal perforated metallic shield disc, (FIG. 3)
Gas: Oxygen (Pure)
Power Density: 0.015 W/cm$^3$

| Flow Rate (scc/min) | Pressure (torr) | Exposure (min) | Resultant Microbial Count (CFUs) | Percent Kill(%) |
|---|---|---|---|---|
| 30 | 0.20 | 20 | 5.8 × 10$^5$ | 77.6923 |
| 30* | 0.22 | 45 | <10 | 99.9999 |

Temperature: 24–30° C.
*Sample enclosed in barrier cloth, 2-ply, American Textiles, Inc.
Pyrex chamber dimensions: 6"D × 10"L

EXAMPLE 12

With Pyrex chamber and two uncooled internal Perforated cylinders, (FIG. 1)
Gas: O$_2$
Flowrate 70 scc/min
Pressure: 0.275 torr
Power Density: 0.016 W/cc
Exposure Time: 45 min
Temperature: 92° C.
Percent Kill: Total Kill
Pyrex chamber dimensions: 9"D×13"L
Sample was the standard sterilization test Pack provided by guidelines of the Association for the Advancement of Medical Instrumentation (AAMI)

EXAMPLE 13

With Pyrex chamber and two cooled internal perforated cylinders, (FIG. 1)
Same experimental conditions as in Example 12
Temperature: 54° C.
Percent Kill: Total Kill
Sterilization test pack employed was according to AAMI guidelines.

EXAMPLE 14

With Pyrex chamber and uncooled internal perforated cylinder
Gas: O$_2$
Flowrate 70 scc/min
Pressure: 0.275 torr
Power Density: 0.014 W/cc
Exposure Time: 30 min
Temperature: 85° C.
Percent Kill: Total Kill
Pyrex chamber dimensions: 9"D×13"L

EXAMPLE 15

With Pyrex chamber and cooled internal perforated cylinder, (FIG. 1)
Same experimental conditions as in Example 14
Temperature: 47° C.
Percent Kill: Total Kill
Pyrex chamber dimensions: 9"D×13"L

EXAMPLE 16

With Pyrex chamber and cooled internal Perforated cylinder, (FIG. 1)
Same experimental conditions as in Example 14
Exposure time: 2 ¼ hr.

Temperature: 51° C.
Percent Kill: Total Kill
Pyrex chamber dimensions: 9"D×13"L

EXAMPLE 17

With Pyrex chamber and uncooled internal perforated cylinder
Gas: $O_2$ (containing 500 ppm of $H_2O$)
Flowrate: 70 scc/min
Pressure: 0.275 torr
Power Density: 0.015 W/cc
Exposure Time: 20 min.
Temperature: 61° C.
Percent Kill: Total Kill
Pyrex Chamber Dimensions: 9"D×13"L

EXAMPLE 18

With Pyrex chamber (9"D×13"L) and cooled internal Perforated metallic cylinder, (FIG. 1)
Gas: Dry and moist Oxygen, Nitrogen and Argon ($H_2O$ level: 300 ppm)
Flowrate: 100 scc/min
Pressure: 0.280-0.300 torr
RF Power Density: 0.020 W/cc
Temperature: 38°-57° C.
Sample Size per Experiment: Ten (10) 3M "Attest" vials with $4\times10^6$ spores/strip in each vial, placed in a sealed Tyvek/polyethylene pouch.

| Exposure Time (min) | Dry $O_2$ | Moist $O_2$ |
| --- | --- | --- |
| 30 | 4 vials - total kill | 9 vials - total kill |
| 45 | 6 vials - total kill | 10 vials - total kill |
| 60 | 8 vials - total kill | — |
| 75 | 10 vials - total kill | — |
|  | Dry $N_2$ | Moist $N_2$ |
| 30 | 0 vials - total kill | 0 vials - total kill |
| 45 | 0 vials - total kill | 0 vials - total kill |
| 60 | 1 vial - total kill | 2 vials - total kill |
| 75 | 2 vials - total kill | 3 vials - total kill |
|  | Dry Ar | Moist Ar |
| 30 | 0 vials - total kill | 0 vials - total kill |
| 45 | 0 vials - total kill | 1 vial - total kill |
| 60 | 1 vial - total kill | 2 vials - total kill |
| 75 | 2 vials - total kill | 3 vials - total kill |

EXAMPLE 19

With Pyrex chamber (9"D×13"L) and cooled internal metallic perforated cylinder, (FIG. 1)
Gas: $O_2$
Flowrate: 100 scc/min
Pressure: 0.280 torr
RF Power Density: 0.020 W/cc
Exposure time: 70-105 min
Temperature: 50° C.
Samples:
  a. 24-inch long PVC tubing with internal diameter of 11 mm and wall thickness of 2 mm.
  b. 24-inch long silicone rubber tubing with internal diameter of 3/16" and wall thickness of 1/16".
Spore strip was placed in middle of tubing at approximately 18-inch from either free end of tubing. The latter was bent into a U-shape and placed within a Tyvek/polyethylene pouch and sealed prior to plasma sterilization.
Percent Kill: Total Kill

EXAMPLE 20

With Pyrex chamber (9"D×13"L) and cooled internal Perforated metallic cylinder, (FIG. 1)
Gas: Dry and Moist Nitrogen-Oxygen and Argon-Oxygen Mixtures ($O_2$:5-15%);
($H_2O$ level: 300 Ppm)
Flowrate: 100 scc/min
Pressure: 0.275-0.300 torr
RF Power Density: 0.020 W/cc
Temperature: 34°-53° C.
Sample Size per Experiment: Ten (10) 3M "Attest" vials with $4\times10^6$ spores/strip in each vial, placed in a sealed Tyvek/polyethylene pouch

| Exposure Time (min) | Dry $N_2$—$O_2$ | Moist $N_2$—$O_2$ |
| --- | --- | --- |
| 30 | 1 vial - total kill | 1 vial - total kill |
| 45 | 1 vial - total kill | 1 vial - total kill |
| 60 | 2 vials - total kill | 3 vials - total kill |
| 75 | 3 vials - total kill | 4 vials - total kill |
|  | Dry Ar—$O_2$ | Moist Ar—$O_2$ |
| 30 | 1 vial - total kill | 1 vial - total kill |
| 45 | 1 vial - total kill | 2 vials - total kill |
| 60 | 3 vials - total kill | 4 vials - total kill |
| 75 | 4 vials - total kill | 5 vials - total kill |

I claim:

1. A method for sterilization and treatment of medical and dental devices and materials comprising the steps of,
placing said devices and materials on a generally planar metallic electrode, said planar electrode being positioned within a gas-tight confining chamber, said chamber being made of metal and connected to a point of potential reference, the internal surface area of said chamber being substantially larger than the surface area of said planar electrode,
further including a perforated metallic enclosure within said chamber, said perforated enclosure being insulated from, but surrounding and containing said planar electrode and said devices and materials positioned thereon, said enclosure being connected to said point of potential reference,
evacuating said chamber to a substantially low pressure and introducing a gas into said chamber wherein said gas comprises water vapor in excess of 100 ppm in a binary mixture with any one of the groups of gases consisting of oxygen, nitrogen, argon or a halogen,
initiating an electrical discharge in said gas within said chamber by application of an RF voltage between said planar electrode and said point of potential reference creating a gas plasma,
maintaining said gas plasma for a controlled period of time,
maintaining a flow of said gas through said chamber, and
withdrawing said devices and materials from said chamber.

2. A method for sterilization and treatment of medical and dental devices and materials comprising the steps of,
placing said devices and materials within a first metallic perforated electrode, said electrode being positioned within, and spaced from a fluid cooled metallic gas-tight confining chamber with a wall connected to a point of potential reference, evacuating said chamber to a substantially low pressure and introducing a gas into said chamber, wherein said gas is selected from the group consisting of, an oxidizing gas, a reducing gas, and a gaseous mixture of oxygen and any one of the gases consisting of, nitrogen, argon, helium or halogen, initiating an electrical discharge in said gas within said chamber by application of an RF voltage between said internal perforated electrode and the chamber wall, creating a gas plasma accompanied by a substantially field free and glowless volume within the perforated electrode containing said devices and materials, whereby said devices and materials are contacted by substantially electrically neutral active species at a temperature below that which would be detrimental to said devices and materials, maintaining said gas plasma for a controlled period of time, maintaining a flow of said gas through said chamber; and withdrawing said devices and materials from said chamber.

3. A method for sterilization and treatment of medical and dental devices and materials comprising the steps of, placing said devices and materials on a generally planar metallic electrode, said electrode being positioned within a gas-tight fluid cooled confining chamber, said chamber being made of metal and connected to a point of potential reference, the internal surface area of said chamber being substantially larger than the surface area of said planar electrode, further including a perforated metallic enclosure within said chamber, said perforated enclosure being insulated from, but surrounding and containing said planar electrode and said devices and materials positioned thereon, said enclosure being connected to said point of potential reference, evacuating said chamber to a substantially low pressure and introducing a gas into said chamber, initiating an electrical discharge in said gas within said chamber by application of an RF voltage between said planar electrode and said point of potential reference creating a gas plasma, maintaining said gas plasma for a controlled period of time, maintaining a flow of said gas through said chamber; and withdrawing said devices and materials from said chamber.

4. Apparatus for sterilization and treatment of medical and dental devices and materials in a gas plasma comprising, a gas-tight confining chamber having a metallic wall, said chamber wall being connected to a point of potential reference, a fluid cooled internal planar electrode positioned within said chamber, a perforated metallic enclosure insulated from, and containing said planar electrode, said perforated metallic enclosure being connected to said point of potential reference, means for applying an RF voltage between said planar electrode and said point of potential reference, means for connecting to and evacuating said chamber, and means for connecting to and flowing gas through said chamber.

5. Apparatus in accordance with claim 4 wherein said gas-tight confining chamber is fluid cooled.

6. A method for sterilization and treatment of medical and dental devices and materials comprising the steps of, placing said devices and materials within a first perforated metallic electrode, said electrode being positioned within, and spaced from a gas-tight confining chamber with a wall, said chamber being formed of metal and connected to a point of potential reference, evacuating said chamber to a substantially low pressure and introducing a gas into said chamber, initiating an electrical discharge in said gas within said chamber by application of an RF voltage between said perforated metallic electrode and the metallic chamber wall, creating a gas plasma accompanied by a field-free and glowless volume within the perforated electrode containing said devices and materials, whereby said devices and materials are contacted by substantially electrically neutral active species at a temperature below that which would be detrimental to said devices and materials, wherein said gas comprises water vapor in excess of 100 ppm in a binary mixture with any one of the groups of gases consisting of, oxygen, nitrogen, argon or a halogen, maintaining said gas plasma for a controlled period of time, maintaining a flow of said gas through said chamber; and withdrawing said devices and materials from said perforated electrode within said chamber.

7. A method in accordance with claim 6 wherein said devices and materials are enclosed within sealed pouches formed of gas permeable materials while in said chamber.

8. Apparatus for sterilization and treatment of medical and dental devices and materials in a gas plasma comprising, a gas-tight confining chamber with a wall, a first liquid cooled perforated metallic electrode positioned within and spaced from said chamber wall, means for applying an RF voltage between said perforated electrode and said chamber wall, means for connecting to and evacuating said gas-confining chamber, means for connecting to and flowing gas through said chamber, and a liquid cooling system fluidically isolated from said means for flowing gas through said chamber, for cooling said first perforated electrode.

9. Apparatus for sterilization and treatment of medical and dental devices and materials in a gas plasma comprising, a gas-tight confining chamber, a first liquid cooled perforated metallic electrode, said electrode being positioned within and spaced from said gas-tight confining chamber, a second perforated metallic electrode positioned between and spaced apart from said gas-tight chamber and said first perforated electrode, means for evacuating said chamber, means for flowing gas through said chamber, a liquid cooling system fluidically isolated from said means for flowing gas through said chamber, for cooling said first perforated electrode, and means for applying an RF voltage between said second perforated electrode and said gas-confining chamber wall.

10. Apparatus in accordance with claim 9 wherein said second perforated metallic electrode is fluid cooled.

11. Apparatus for sterilization and treatment of medical and dental devices and materials in a gas plasma comprising, a gas-tight confining chamber, a first liquid cooled perforated metallic electrode positioned within and spaced from said chamber wall, means for electrically connecting said chamber wall to a point of potential reference, means for applying an RF voltage between said perforated electrode and said point of potential reference, mean for evacuating said gas-confining chamber, means for flowing gas through said chamber, and a liquid cooling system fluidically isolated from said means for flowing gas through said chamber, for cooling said first perforated electrode.

12. Apparatus for sterilization and treatment of medical and dental devices and materials in a gas plasma comprising, a gas-tight confining chamber formed with a metallic wall connected to a point of potential reference, a first fluid cooled perforated metallic electrode connected to a point of potential reference, said electrode being positioned within and spaced from said gas-tight confining chamber, a second perforated metallic electrode positioned between and spaced apart from said gas-tight chamber and said first perforated electrode, means for evacuating said chamber, means for flowing gas through said chamber, a fluid cooling system fluidically isolated from said means for flowing gas through said chamber, for cooling said first perforated electrode, and means for applying an RF voltage between said second perforated metallic electrode and said point of potential reference.

13. Apparatus in accordance with claim 12 wherein said second perforated metallic electrode is fluid cooled.

14. Apparatus in accordance with any one of claims 8, 9, 11, 12, 10 or 13 wherein said gas tight confining chamber is fluid cooled.

15. A method for sterilization and treatment of medical and dental devices and materials comprising the steps of, placing said devices and materials within a first metallic perforated electrode, said electrode being positioned within, and spaced from a fluid cooled gas-tight confining chamber with a wall, evacuating said chamber to a substantially low pressure and introducing a gas into said chamber, initiating an electrical discharge in said gas within said chamber by application of an RF voltage between said internal perforated electrode and the chamber wall, creating a gas plasma accompanied by a substantially field-free and glowless volume within the perforated electrode containing said devices and materials, whereby said devices and materials are contacted by substantially electrically neutral active species at a temperature below that which would be detrimental to said devices and materials, maintaining said gas plasma for a controlled period of time, maintaining a flow of said gas through said chamber; and withdrawing said devices and materials from said chamber.

16. A method in accordance with claim 15 wherein said gas tight chamber is metallic and is connected to a point of potential reference.

17. A method in accordance with either of claims 15 or 16 wherein said devices and materials are enclosed within sealed pouches formed of gas permeable material while said pouches containing said materials and devices are within said chamber.

18. A method in accordance with either of claims 15 or 16 wherein said gas comprises one or more of the group of gases consisting of:

hydrogen; oxygen; nitrogen; hydrogen-oxygen mixtures; hydrogen-oxygen-inert gas mixtures; oxygen-nitrogen mixtures; oxygen-nitrogen-inert gas mixtures; nitrogen-hydrogen mixtures; nitrogen-hydrogen-inert gas mixtures; oxygen-nitrogen-hydrogen mixtures; oxygen-nitrogen-hydrogen-inert gas mixtures; oxygen-helium mixtures; oxygen-organohalogen mixtures; oxygen-organohalogen-inert gas mixtures; oxygen-organohalogen-nitrogen mixtures; oxygen-inorganic halogen mixtures; oxygen-inorganic halogen-inert gas mixtures; oxygen-inorganic halogen-nitrogen mixtures; oxygen-inorganic oxyhalogenated compound mixtures; oxygen-inorganic oxyhalogenated compound-inert gas mixtures; oxygen-inorganic oxyhalogenated compound-nitrogen mixtures, helium, argon, helium-argon mixtures.

19. A method in accordance with either of claims 15 or 16 and wherein said gas comprises water vapor in excess of 100 ppm as a constituent in a binary mixture with any one of the groups of gases consisting of oxygen, nitrogen, argon or a halogen.

20. Method according to claim 15 wherein said gas is selected from the group consisting of, an oxidizing gas, a reducing gas, and a gaseous mixture of oxygen and any one of the gases consisting of, nitrogen, argon, helium or halogen.

21. Method according to claim 20 wherein said first perforated electrode is fluid cooled.

22. A method for sterilization and treatment of medical and dental devices and materials comprising the steps of, placing said devices and materials within a first fluid cooled metallic perforated electrode, said electrode being positioned within, and spaced from a gas-tight confining chamber with a wall, evacuating said chamber to a substantially low pressure and introducing a gas into said chamber, wherein said gas is selected from the group consisting of, an oxidizing gas, a reducing gas, and a gaseous mixture of oxygen and any one of the gases consisting of, nitrogen, argon, helium or halogen, initiating an electrical discharge in said gas within said chamber by application of an RF voltage between said internal perforated electrode and the chamber wall, creating a gas plasma accompanied by a substantially field-free and glowless volume within the perforated electrode containing said devices and materials, whereby said devices and materials are contacted by substantially electrically neutral active species at a temperature below that which would be detrimental to said devices and materials, maintaining said gas plasma for a controlled period of time, maintaining a flow of said gas through said chamber; and withdrawing said devices and materials from said chamber.

23. A method for sterilization and treatment of medical and dental devices and materials comprising the steps of, placing said devices and materials within a first fluid cooled metallic perforated electrode, said electrode being positioned within and spaced from a gas-tight confining chamber with a wall, said chamber enclosing a fluid cooled second perforated metallic electrode positioned between and spaced apart from said gas-tight chamber and said first perforated electrode, evacuating said chamber to a substantially low pressure and introducing a gas into said chamber, wherein said gas is selected from the group consisting of, an oxidizing gas, a reducing gas, and a gaseous mixture of oxygen and any one of the gases consisting of, nitrogen, argon, helium or halogen, initiating an electrical discharge in said gas within said chamber by application of an RF voltage between said second perforated electrode and said chamber wall, creating a gas plasma accompanied by a substantially field-free and glowless volume within said first perforated electrode containing said devices and materials, whereby said devices and materials are contacted by substantially electrically neutral active species at a temperature below that which would be detrimental to said devices and materials, maintaining said gas plasma for a controlled period of time, and maintaining a flow of said gas through said chamber; withdrawing said devices and material from said first perforated electrode.

24. A method in accordance with either of claims 22 or 23 wherein said gas-tight chamber is metallic and is connected to a point of potential reference.

25. A method in accordance with any one of claims 22, 20 or 21 wherein said devices and materials are enclosed within sealed pouches formed of gas permeable materials while in said chamber.

26. A method for sterilization and treatment of medical and dental devices and materials comprising the steps of, placing said devices and materials on a generally planar fluid cooled metallic electrode, said electrode being positioned within a gas-tight confining chamber, said chamber being made of metal and connected to a point of potential reference, the internal surface area of said chamber being substantially larger than the surface area of said planar electrode, further including a perforated metallic enclosure within said chamber, said perforated enclosure being insulated from, but surrounding and containing said planar electrode and said devices and materials positioned thereon, said enclosure being connected to said point of potential reference, whereby said devices and materials are contacted by a substantially electrically neutral active species at a temperature below that which would be detrimental to said devices and materials, evacuating said chamber to a substantially low pressure and introducing a gas into said chamber, wherein said gas is selected from the group consisting of, an oxidizing gas, a reducing gas, and a gaseous mixture of oxygen and any one of the gases consisting of, nitrogen, argon, helium or halogen, initiating an electrical discharge in said gas within said chamber by application of an RF voltage between said planar electrode and said point of potential reference creating a gas plasma, maintaining said gas plasma for a controlled period of time, maintaining a flow of said gas through said chamber; and withdrawing said devices and materials from said chamber.

27. Method in accordance with either one of claims 23 or 26 wherein said gas tight confining chamber is fluid cooled.

* * * * *